Figure 2:
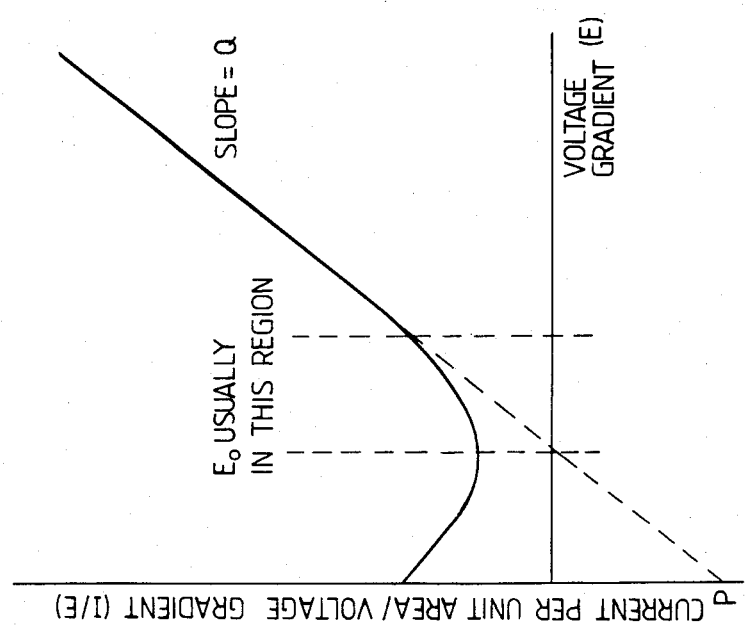

United States Patent [19]

Stangroom

[11] Patent Number: 4,502,973
[45] Date of Patent: Mar. 5, 1985

[54] ELECTROVISCOUS FLUIDS

[75] Inventor: James E. Stangroom, Castleton, England

[73] Assignee: National Research Development Corporation, London, England

[21] Appl. No.: 466,337

[22] PCT Filed: Jun. 18, 1982

[86] PCT No.: PCT/GB82/00183

§ 371 Date: Feb. 3, 1983

§ 102(e) Date: Feb. 3, 1983

[87] PCT Pub. No.: WO82/04442

PCT Pub. Date: Dec. 23, 1982

[30] Foreign Application Priority Data

Jun. 19, 1981 [GB] United Kingdom ............... 8118885

[51] Int. Cl.³ .......................... H01B 3/24; C09K 3/00
[52] U.S. Cl. ..................................... 252/73; 252/78.1;
252/581; 524/363; 524/371; 524/393; 556/465;
556/489; 568/27; 568/28; 568/34; 568/35;
568/56; 568/58; 568/639; 570/182; 570/184
[58] Field of Search ................ 252/73, 78.1, 581;
524/363, 371, 393; 556/465, 489; 568/27, 28,
34, 35, 56, 58, 639; 570/182, 184

[56] References Cited

U.S. PATENT DOCUMENTS

| | | | |
|---|---|---|---|
| 2,165,813 | 7/1939 | Prutton | 252/581 |
| 3,402,204 | 9/1968 | Plummer et al. | 568/34 |
| 3,472,782 | 10/1969 | Nowotny | 568/639 |
| 4,033,892 | 7/1977 | Stangroom | 252/76 |
| 4,118,363 | 10/1978 | Smith | 524/371 |
| 4,260,506 | 4/1981 | Munch et al. | 252/581 |

FOREIGN PATENT DOCUMENTS 1570234 6/1980 United Kingdom.

*Primary Examiner*—Paul Lieberman
*Assistant Examiner*—Robert A. Wax
*Attorney, Agent, or Firm*—Cushman, Darby & Cushman

[57] ABSTRACT

Electroviscous (EV) fluids consisting of solid hydrophilic particles dispersed in hydrophobic liquids, where the liquid contains a diaryl derivative component of general formula I

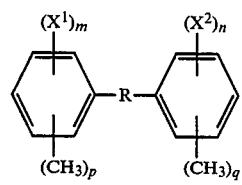

in which R is $CY_2, O, S, SO, SO_2, SiF_2$, or $O-SiY_2-O$, $X^1$ and $X^2$ are halogens, $(m+n)$ is between 1 and 3 on average, and $(p+q)$ is between 0 and 1 on average. EV fluids containing these novel components possess generally improved properties in terms of lower viscosities, electrical conductivities, toxicities and freezing points. In a preferred embodiment, the component is a mixture of brominated diphenyl methanes in which R is $CH_2, n=0, X^1=Br, (m+n)$ is approximately one, and $(p+q)=0$.

14 Claims, 2 Drawing Figures

ELECTROVISCOUS FLUIDS

This invention relates to electroviscous (EV) fluids.

Electroviscous fluids are suspensions of finely divided hydrophilic solids in hydrophobic liquids. When an electric field is applied to such a suspension, it changes from an approximately Newtonian material to a Bingham plastic. The change is very rapid and reversible. The currents passed are extremely low. Such fluids may hence be used as an interface between electronics and power hydraulics.

The hydrophilic solids used in EV fluids have been much studied, for example see UK Pat. No. 1,501,635. The liquid components of such fluids have been much less studied. Some desirable properties of a base liquid may be summarised as follows:

1. High boiling point and low freezing point, giving the EV fluid a wide temperature range (ideally ca −40° C. to 200° C.) and low vapour pressure at normal working temperatures.

2. Low viscosity, to give the fluid a low no-field viscosity.

3. High electrical resistance and high dielectric strength, to ensure that the fluid draws little power in operation and may be used over a wide range of applied field strengths.

4. High density (generally greater than 1.2 and typically 1.3–1.6 g/ml) since it is preferable for the EV solid and liquid components to have the same density, to prevent settling on standing.

5. Chemical stability.

It should also be of relatively low cost and toxicity and preferably bio-degradeable.

There appear, moreover, to be other more subtle physico-chemical factors involved in determining whether a liquid is suitable. Synergistic effects occur, and it is found that although two liquids may separately give good EV fluids they may not do so when mixed and certain liquids may be effective only with certain solids. These chemical features are not yet understood.

In practice it is difficult to combine the above requirements in a single liquid, and some of these properties tend to be mutually exclusive. The most difficult objective to achieve is chemical stability without environmental persistence and a consequential pollution hazard: there is at present legislation restricting the use of persistent materials and this legislation is likely to increase. Although EV devices can be constructed so as to be totally enclosed, it would seem to be a retrograde step to introduce another commercial use for suspect materials.

Of the three types of materials used at present as EV liquids, hydrocarbons, certain fluorinated polymeric materials and polychlorinated biphenyls, none is entirely suitable. Hydrocarbons suffer from the disadvantages of low density and the difficulty of combining high boiling points with low viscosities. The fluorinated materials which have been considered, such as the trifluoro-chloro-ethylene polymer 'Fluorolube' suffer from the disadvantages of environmental persistence, high cost, and a tendency to be immiscible with other liquids which might otherwise be used as inert diluents to achieve density matching with EV solids. Polychlorinated biphenyls have high viscosities and additionally have been recognised as dangerous pollutants.

It is one object of the present invention to provide an EV fluid that employs a liquid component that meets more fully the desirable characteristics listed above.

Other objects and advantages will become apparent from the description set out below.

According to the present invention there is provided an electroviscous fluid comprising a hydrophilic solid and hydrophobic liquid component wherein the hydrophobic liquid component comprises at least one diaryl derivative of general formula I

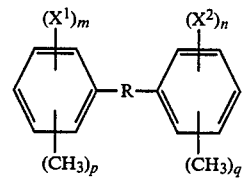

wherein R is $CY_2$, O, S, $SO_2$, Si $F_2$ or $O-Si(Y_2)-O$, $X^1$ and $X^2$ are either the same or different and are F, Cl or Br, each of m and n is 0, 1, 2 or 3, each of p and q is 0, 1 or 2 and Y is H, F or a methyl or ethyl group, provided that, for the said diaryl derivatives in the liquid component, the average value of (m+n) is from 1 to 3 inclusive and the average value of (p+q) is from 0 to 1 inclusive.

The term "average value" as used above refers to the sum of (m+n) or (p+q) values for each molecule of diaryl derivative in the liquid component divided by the number of molecules of diaryl derivative in the liquid component.

Preferably R is $CH_2$, O or S, $X^1$ and $X^2$ are either the same or different and are Cl or Br, each of m and n is 0, 1 or 2, and each of p and q is 0 or 1. In a particularly preferred embodiment of the hydrophobic liquid component of the present invention R is $CH_2$, $X^1$ and $X^2$ are Br, each of m and n is 0, 1 or 2, each of p and q is 0 and the average value of (m+n) is about 1. This preferred material is referred to hereinafter as Bromodiphenyl methane (BDM).

Preferably a substantial proportion (more than 80%) of the diaryl derivatives in the liquid component are asymmetrically substituted.

The molar volume (gm molecular weight/density) of the liquid component should preferably be above about 120cm$^3$.

EV liquid components according to the invention combine most of the desirable properties described above. The interposition between the rings of small groups or atoms of the type described allows free rotation of the rings and hence a low viscosity, generally around 15–20 mPa.s at 20° C. (BDM=15 mPa.s at 20° C.), compared with the conventional biphenyl derivatives, while maintaining a high density. At 20° C., diaryl derivatives of general formula I wherein R is $CH_2$ generally have densities of about 1.2–1.64 g/m$^3$, (BDM=1.45 g/m$^3$) and if R is O of about 1.32–1.8 g/cm$^3$, entirely compatible with many EV solids.

The introduction of groups containing benzyl-type carbon atoms, or heteroatoms between the rings, enables them to be degraded by biological processes, and therefore reduces any pollution hazard. The materials are however generally chemically stable and may be stored without deterioration. Some of the derivatives wherein R=CH$_2$ tend to darken from their original water-white or lemon yellow colour on exposure to light, but without any deletrious effect on their EV suitability. This discolouration may easily be removed by distillation or passage through activated alumina.

Some of the thio-ether based materials (R=S) may be susceptible to oxidation. Some sulphone (R=SO) and sulphoxide (R=SO$_2$) based materials are solids at ambient temperatures, and therefore unsuitable for use in the present EV fluid. Others however are stable liquid materials and hence suitable for use.

The asymmetric diaryl derivatives of this invention have lower freezing points than their symmetric counterparts. This effect is very marked and is a significant advantage of the preferred aspect of this invention. The effect is especially pronounced in the monomethyl substituted diphenyl methane derivatives (p or q=1) resulting in a drop of some 60° C. in the freezing point below that of the corresponding unsubstituted diphenyl methane derivatives. It has been found that additional methyl groups on the ring do not further depress the freezing point, and have a disadvantageous effect in reducing the density. One methyl group therefore appears to be an optimum degree of substitution. In addition, the introduction of asymmetry into the molecule tends to increase the bio-degradability for reasons which are not entirely understood.

Liquid materials according to the invention may be prepared by conventional synthetic methods. Materials wherein R is CH$_2$, CH.CH$_3$ or O may for example be prepared by direct halogenation of, for example, diphenyl methanes, 1, 1 diphenyl ethanes or biphenyl ethers using either the elemental halogen in the presence of a suitable catalyst, if necessary, sulphuryl chloride or phosphorus pentachloride. These direct methods tend to give products containing interfering impurities resulting particularly from halogenation of CH$_2$ as well as the ring positions and indirect syntheses, giving more controllable products, are to be preferred. However, liquid components, produced by direct halogenation, and containing impurities such as non-halogenated diphenyl methanes and/or diphenyl methyl halides are within the scope of the present invention.

Suitable indirect syntheses include for example the Schnick Reaction (J W Schick—U.S. Pat. No. 3,028,436) in which two molecules of a substituted phenyl group are condensed with formaldehyde (used in the form of paraformaldehyde) to create a-CH$_2$-bridged diphenyl methane derivative. Such materials may also be prepared via for example reduction and diazotisation reactions starting from 2, 2$^1$, 4, 4$^1$, tetranitro-diphenyl-methane which is an easily prepared starting reagent (see for example K Matsumura: JACS 51, 816, (1929)). Using this route, and via Gatterman, Sandmeyer or Balz and Schliemann reactions a variety of halo-substituted diphenyl-methane derivatives may be obtained.

A preferred method of preparation of materials according to the invention is by a Friedel-Crafts reaction, as this allows the maximum flexibility of choice of ring-systems to be joined and gives the most easily controllable products with the least number of substitution alternatives. Friedel-Crafts reactions are notoriously sensitive in their yield and freedom from side reactions to the exact reaction conditions, and therefore these must be carefully controlled to give an optimum product.

Liquids in which R is CF$_2$ may be prepared for example by exchanging fluorine for chlorine in dichlorodiphenyl methane, made from benzophenone and phosphorus pentachloride, using antimony trifluoride activated with bromine:

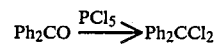

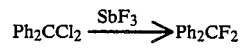

Alternatively, fluorinated materials may be prepared using PhSF$_3$, made from PhSSPh and AgF$_2$. This reaction may be carried out at ambient pressure in glass apparatus. Both these reactions are described in Hasek W. R, Smith W C and Engelhardt V A - "The Chemistry of Sulphur Tetrafluoride II: The Fluorination of Organic Carbonyl Compounds" JACS, 82, 543 (1960).

Some silicon-based materials, for example, diphenyl difluorosilane, are commercially available. Dimethyl diphenylsilane may be made via a Grignard type reaction using dimethyl chlorosilane and excess phenyl magnesium bromide. By the reaction of dimethyl chlorosilane with phenol, dimethyl diphenoxy silane may be prepared. These silicon-based materials may be somewhat susceptible to hydrolysis. Other compounds for use in the invention may be prepared by analogous routes.

Most of these reactions produce a number of stereoisomers and side products but often it has been found that it is not necessary to separate these as they do not interfere with the efficiency of the liuqids in EV fluids. It is in fact in some cases advantageous to leave these stereoisomers etc in the liquid, as they have a desirable effect on the colligative properties of the liquid in lowering the freezing point and raising the boiling point. Where necessary though, the materials may easily be purified by the conventional techniques of fractional distillation, molecular distillation etc.

The hydrophobic liquid component of the present invention may consist of a single diaryl derivative or a mixture of diaryl derivatives. In either case the liquid component may also contain other suitable non-conducting oleaginous liquids, either commercially available liquids, such as for example polymers of trifluorovinyl chloride (e.g. Fluorolube F5 - S) or polychlorinated biphenyls (e.g. Aroclor 1242), or other compatible and miscible liquids, the addition of the further liquid being designed to achieve a desired density or viscosity etc. The diaryl derivatives of the present invention are not completely miscible with all such further diluents, and show miscibility ranges which are sensitive to temperature so that care must be taken to select mixtures miscible throughout the desired range of working temperature.

Liquids may be made up into electroviscous fluids according to to the invention with a wide variety of hydrophilic solids, including the solid particulate polyhydric alcohols such as the monosaccharide polymers described in UK Pat. No. 1,501,635 (U.S. Pat. No. 4,033,892), or the water containing polymer particles having free or neutralized acid groups described in UK Pat. No. 1,570,234, (U.S. Pat. No. 4,129,513). The contents of both UK and U.S. patents are incorporated herein by reference. Both the cross-linked and un-cross linked forms of the lithium polymethacrylate polymer salt described in UK Pat. No. 1,507,234 give good EV solids with similar performances when used with the liquids of the invention, but the cross-linked lithium polymethacrylate polymer salt, especially cross-linked with methylene bis-acrylamide (MBA) and preferably in about a 1:6 molar ratio to the methacrylic acid content, is preferred, as EV fluids prepared using this solid have greater long term stability than those prepared using the un-cross linked solid.

The water content of the hydrophilic solid also effects the EV performance of fluids. This phenomenon is discussed in the above mentioned patents. Since the solids are hygroscopic and swell to form gel-like materials in water, precise measurements of water content are extremely difficult and the definition of a true dry state impossible. Water content may be related, as in UK Pat. No. 1,570,234, to an arbitrary "dry" state as achieved by drying in vacuo at 50°–60° C. However, a more useful measure of water content may be derived from the current/voltage relationship of the EV fluid. Thus, as further described below, beyond a certain voltage gradient (or voltage across a given gap) the relationship of (dc current per unit area/voltage gradient across the working gap) to voltage gradient is linear having a slope termed Q. For a given solid/liquid combination log Q is linearly related to water content beyond the arbitrary dry state and hence Q may be used as a practical measure of water content.

With high water content (high Q) fluids the EV response (change in yield point per unit voltage applied) is high up to a limit, the threshold voltage $E_o$ (the voltage above which EV effects are observed) is low, and the response to changes in the applied field is rapid. The current passed though is high. Very high water contents however produce fluids with high viscosities in the absence of an applied field ("no-field" viscosity) and with a low working range of voltage, as arcing occurs at lower voltages. Such very high water content fluids are therefore undesirable.

With fluids of low water content (low Q) the currents passed are low, the range of working voltage is large, and the no-field properties are good. The threshold voltage is however high, and the response to changes in the applied field is slow. Low water content fluids also have an increased tendency to exhibit rheopexy, i.e. the increase of the yield point of the fluid when the fluid is gently agitated. In EV Fluids rheopexy occurs as particles which loosely adhere in a random fashion under the influence of an applied field are compacted under gentle agitation. This effect can cause inconsistencies in measurements of the EV response.

For static (e.g. clutch) applications high and low water content fluids show similar EV responses, but as low water content fluids (Q=0 to 1) pass less current, they are generally preferable. For dynamic (e.g. damper) applications, i.e. for retardation of a system in which the fluid is already being sheared when the voltage is applied, high water content fluids (Q=10 and above) are generally more suitable than low water fluids. The EV effect in low water content fluids becomes unreliable in dynamic situations as such fluids have a higher static than dynamic yield-point, tend to suffer from hysteresis effects and forms of "stick slip". This results in juddering.

The volume fraction of solid used in the EV fluid will depend on the viscosity of the base liquid. In practice the limiting factor in determining the amount of solid used is the increasing viscosity, accompanied by non-Newtonian behaviour at high solid contents. With suitable liquids and suitably treated solids, volume fractions as high as 50% solids may be used. Detectable EV activity may be found at as low as 10% (v/v) solids, but not only are such fluids very feeble, the electrical power input in relation to the mechanical change resulting is also much higher than when the solids content is higher. A solids content of 25–35% by volume has been found to be generally most suitable when the liquids of the present invention are used. The particle size of the solids is preferably between 1 and 50 microns.

A preferred electroviscous fluid composition comprises a 30% v/v suspension of lithium polymethacrylate cross-linked with methylene bis acrylamide, in Bromo-Diphenyl Methane. The fluids will also contain small amounts of water as understood in the art and discussed in the above UK Pat. Nos. 1,501,635 and 1,570,234.

Figure 1:
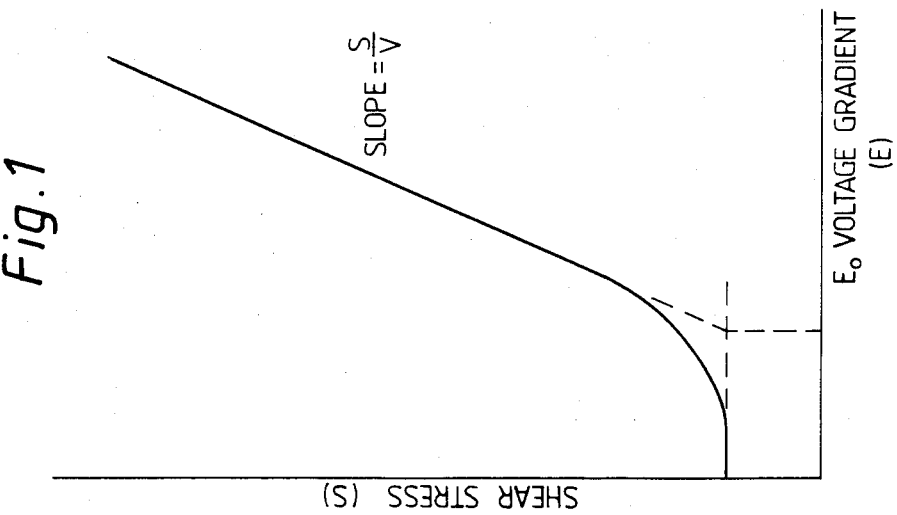

The preparation and properties of hydrophobic liquids according to the invention, and the electroviscous fluids prepared using these liquids will now be illustrated by way of example only with reference to the accompanying drawing in which FIG. 1 shows the relationship of shear strength (S) to applied voltage gradient (E) at zero shear, for an EV fluid according to this invention.

FIG. 2 shows the relationship of (current per unit area (I)/ voltage gradient) to the voltage gradient at zero shear, for an EV fluid according to this invention.

Measurements of electroviscous response were carried out at zero shear using the test rig described in UK Pat. No. 1,501,635 with an electrode gap of 0.5 mm and an electrode area of 78 cm$^2$. 30% v/v MBA cross-linked lithium polymethacrylate was used in all cases as a standard solid, and was ball-milled and sieved to remove all particles greater than 50 microns diameter before use. In order to over come the problems of variable water content of the solid, the EV activity of each fluid prepared using the liquids of the invention was compared with that of a control fluid using a polychlorinated biphenyl, (Aroclor 1242-Trade Mark) prepared simultaneously using the same solid sample.

The EV performance of fluids using the liquids prepared in the examples below are expressed in terms of the threshold voltage gradient Eo and the electroviscous response S/V, both shown in FIG. 1, and the two parameters P and Q which relate the dc current passed by the fluid to the voltage gradient E, as shown in FIG. 2.

The shear stress, S, of a fluid is related to the voltage gradient E by the linear relationship.

$$S = k(E - Eo)$$

over the working range of the fluids above Eo. The constant k, otherwise termed S/V can hence be determined from the slope of the shear stress/voltage graph, FIG. 1. If E and Eo are in KV/mm and S in KPa, S/V has the units Pa.mm/volt.

The relationship of dc current per unit area, I, to voltage gradient takes the form $$I = PE + QE^2$$

or $$E/I = P + QE$$

This relationship is also substantially linear over the working range of the fluids above Eo. P and Q were therefore obtained directly from the intercept on the $I/E$ axis of the extrapolation of the linear portion of the $I/E$ against E graph FIG. 2 and slope of the graph respectively. If I is expressed in milli-Amps/m² and E in KV/mm as before, the units of P and Q are
P=nano-Amps/V.m
Q=femto-Amps/(Volt)²

All measurements of EV performance reported below were made at a standard temperature of 30° C. In reported experiments P was found to be independent of temperature, but the variation of Q with temperature was found to obey a Boltzman type relationship, i.e.

$$Q_{T_1}/Q_{T_2}=\exp[-E/R(1/T_2)]$$

where $T_1$ and $T_2$ are absolute temperatures, R is the gas constant and E is an energy value approximately intermediate between the energy of a hydrogen bond and an ordinary covalent chemical bond, usually about 70 kJ/mole.

The linear relationship between log Q and the water content of the solid used has been mentioned above.

In the preparative examples below, all temperatures are in degrees centrigrade, and 11 densities in g.cm⁻³ unless otherwise stated.

The materials 'Aroclor 1242', 'Fluorolube' and 'Fomblin' are registered Trade Marks and have the following composition.

Aroclor 1242: a polychlorinated biphenyl fraction, density 1.38 g cm⁻³, viscosity 40 mPa.s marketed by the Monsanto Chemical Corporation.

Fluorolube: a polymer of trifluorovinyl chloride manufactured by the Hooker Chemical Company of New York.

Fomblin: a perfluoropolyether fraction marketed by Montedison

EXAMPLE 1

Direct chlorination of Diphenyl Methane using elemental chlorine

Chlorine gas was passed into diphenyl methane in the presence of a catalyst. A suitable catalyst was found to be pyridine, in the approximate ratio of 1 g pyridine to 20 g of diphenyl methane; other common catalysts, such as aluminium chloride or iron metal, lead to the loss of a great deal of product as a red polymer, while others, such as zinc chloride, were without catalytic action. The reaction was carried out at or slightly above room temperature (the temperature rose sharply at the beginning of the reaction and then slowly fell). The progress of the reaction was followed by periodically weighing the reaction vessel. Under the conditions of the reaction, the first substitution took place on the central carbon atom, and only later into the benzene rings.

When sufficient chlorine gas had been absorbed, the liquid was poured into water, and vigorously stirred. The chlorine atoms attached to the central carbon atom underwent hydrolysis, and the liquid solidified, giving a chlorinated derivative of benzophenone. The solid was collected, and reduced by Clemmensen's method, using hydrochloric acid and amalgamated granulated zinc. By this means, a yellow oil was obtained. The oil was separated from the aqueous phase, and finally purified by molecular distillation (c. 150° C./2 mm Hg), by which means a clear oil, with slight fluorescence was obtained. Chlorine equivalent to three atoms per molecule of diphenyl methane was added initially; the final product, having about one chlorine atom per molecule, had a density of 1.2 g cm⁻³ and viscosity 15 mPa.s at 20° C. The material thus obtained tended to yellow on exposure to light.

EV fluids were made up using this liquid and cross linked lithium polymethacrylate at 30% v/v at two water contents, unmeasured but arbitrarily high and low, and were compared with similar fluids made up using Aroclor. The fluid prepared using the liquid above was found to have a higher Eo than Aroclor and passed an anomalously high current at low voltages, but was otherwise found to give an active fluid. The results are given in Table 2 below.

EXAMPLE 2

Chlorination of Diphenyl Methane using Sulphuryl Chloride

A know weight of diphenyl methane was mixed with sufficient sulphuryl chloride to introduce two chlorine atoms into each molecule of diphenyl methane in the presence of a small amount of aluminium chloride as catalyst, and the mixture was gently warmed. The reaction vessel was wrapped in foil to exclude light. A vigorous reaction occurred indicated by a brisk effervescence of HCl gas. The mixture was boiled under reflux until boiling suddenly ceased, indicating that all the sulphuryl chloride had been consumed. When the reaction was complete the mixture was cooled, shaked with water, and the lower organic layer run off, distilled under vacuum (200° C., 5 mm of mercury) and finally purified by molecular distillation. A water white oil was obtained which had a density of 1.22. The viscosity was considerably lower than Aroclor.

EV fluids were made up with this liquid and the cross-linked lithium polymethacrylate and were found to be quite effective. The results are given in Table 2 below.

EXAMPLE 3

Chlorination of Diphenyl Ether

A volume of diphenyl ether was placed in a tinfoil-wrapped flask, a small quantity of aluminium chloride was added and the flask gentle warmed. A slow stream of chlorine, dried by passage through sulphuric acid was bubbled through the liquid with periodic weighing to monitor the chlorine uptake. When the increase in weight of the flask corresponded to the introduction of three atoms of chlorine per molecule the chlorine stream was stopped, air was readmitted to the system, and the resulting deep red-brown liquid was shaken with aqueous potassium hydroxide (to remove possible phenolic contaminants) and distilled under reduced pressure (ca 5 mm of mercury). Three fractions were collected over the ranges 175°–185° C, 185°–195° C. and 195°–205° C. The lowest fraction was water-white and had a density of 1.32 g cm⁻³. The two higher fractions were progressively deeper yellow and had densities of 1.34 and 1.35 g cm⁻³ respectively. A sample of the lowest fraction was tested for conductivity in a static test rig (78 cm², gap 0.5 mm) and passed 100 microamps at 1 kv. Standing over potassium hydroxide for 48 hours made no difference to this.

The three fractions were pooled and submitted to molecular distillation to obtain a water-white distillate with half the conductivity of the starting material.

The product did not freeze at 5° C. 30% v/v fluids were made up using cross-linked lithium polymethacrylate. As can be seen from Table 2 below the liquid showed a slight increase in Eo, as compared with the parent diphenyl ether, but a worse EV performance than Aroclor. The liquid passed higher currents and gave lower yield points. Comparison of shear rate with the shear stress transmitted across the fluid showed that the chlorinated diphenyl ether materials transmitted considerably less shear stress at the same shear rate.

EXAMPLE 4

Schick Reaction between Chlorobenzene and Formaldehyde in the presence of concentrated Sulphuric Acid. (U.S. Pat. No. 3,028,436 dated Apr. 3, 1962)

500 g of chlorobenzene and 100 g of concentrated sulphuric acid were heated to 100° C., and five 12 g portions of paraformaldehyde added at 30 min intervals over a total of 3 hrs with swirling after each addition to mix the reagents. Water cooling was maintained over this reaction period. At the end of the reaction period, the organic mixture was extracted with water, to remove the acid, and the liquid organic layer distilled at atmospheric pressure. The fraction boiling in the range 300°–350° C. (corresponding roughly to Schick's 'Cut 1' was collected.

For use in EV fluids, the product was further purified, by fractional distillation, using a Vigreux column. The first fraction obtained, up to 320° C., was yellow. Above this, the distillate became water-white, and the fraction boiling in the range 328°–335° C. was collected as the major product. A final, high-boiling fraction was discarded. By refractionating the first, yellow fraction a significant amount of the desired product was obtained, leaving a non-volatile coloured residue in the still-pot. It must be emphasised that the desired product is water-white; the colour of the distillate is the best guide during the distillation.

On cooling, the product deposited a very fine white precipitate, which disappeared on warming. This was removed by slowly cooling the product to 0° C., at which temperature it froze completely, and then allowing the mass to thaw slowly in a filter. The filtrate was clear, and water-white; a small quantity of white, waxy contaminant was left on the filter. In some cases, it was necessary to repeat this freeze-thaw treatment if, by chance, a large amount of contaminant was present. The final liquid was clear, water-white with a very faint fluorescence. Its density was 1.23 g cm$^{-3}$ and its viscosity at 30° C. was about 15 mPa.s. From the amounts quoted (500 g chlorbenzene, 60 g paraformaldehyde), 120 g of the desired product was obtained, but approximately 100 g of chlorobenzene, as its water azeotrope (70% chlorobenzene, BP 90° C.) was recovered unreacted.

EV fluids made up using this liquid and the cross-linked lithium polymethacrylate solid were found to be almost identical in properties to fluids made up using Aroclor and the same solid as shown in Table 2 below.

The liquid was also found to arc at a higher voltage than the Aroclor based fluids. The liquid was found to be miscible with Fluorolube at ambient temperatures to increase its density, but immiscibility occurred at lower temperatures.

EXAMPLE 5

Schick Reaction between Bromobenzene and Formaldehyde

The basic Schick method was applied, without fundamental modification, to the production of a bromo-compound. The actual reaction was carred out exactly as in example 4, save that 697 g of bromobenzene were substituted for the original 500 g of chlorobenzene. The reaction using bromobenzene was noticeably more vigorous than with chlorobenzene, and quite sufficient heat to boil the water-bath used to control the temperature was generated after each addition of paraformaldehyde.

The purification of the bromo-compound differed from that of the chloro-derivative. The cooled reaction mixture was poured into water; addition of a small amount of acetone, to reduce the viscosity of the organic material was found to be advantageous. The organic layer was then washed, first with 1N sodium hydroxide, and thn with water.

Distillation was carried out in several stages. In the first stage, at atmospheric pressure, the material was heated until the temperature of the vapour reached 200° C.; this removed water and unreacted bromobenzene (BP 156° C.). The distillation was then continued under reduced pressure at 6 mm of mercury. After final traces of volatile materials had been eliminated, the temperature of the vapour rose to 220° C., and a water-white distillate was collected. Distillation was continued until the vapour temperature reached 240° C., at which point the distillate became high-melting. It was found to be convenient to use a water-cooled condenser in this distillation in order to readily detect when this high-melting material was evolved. Further distillation, conveniently molecular (174° C./1 mm Hg), was necessary to obtain a water-white product. It has been found that even minor amounts of coloured impurity in the product greatly increase the conductivity of the liquid. The 'freeze-thaw' filtration technique described under Example 4 was advantageously applied to this material, the liquid completely solidifying at about 4° C.; by its use, significant amounts of a white solid were removed.

The final produce had a density of 1.64 g cm$^{-3}$ at 20° C., and an approximate viscosity, at 30° C., of 19 mPa.s. The liquid was found to acquire a yellow tinge on standing. The high density of the liquid enabled density-matched EV fluids to be prepared using suitable solids. EV fluids made using cross-linked lithium polymethacrylate were found to be effective, and comparable with fluids made using Aroclor as shown in Table 2 below. Though fluids using the liquid had a higher Eo than Arclor based fluids, they passed less current.

EXAMPLE 6

Preparation of Bromo Diphenyl Methane 1400 ml of bromobenzene were mixed with 65 g of anhydrous aluminium chloride and the mixture was stirred magnetically. 640 ml of benzyl chloride was added dropwise over approximately four hours, and the mixture left stirring overnight at room temperature. The reaction mixture was then washed three times with 1000 ml 2M NaOH, then three times with 1000 ml water, the aqueous layer being discarded. The organic mixture was then evaporated in a rotary evaporator at 100° C., 12 mm of mercury. The distillate was fractionated to recover re-usable bromobenzene. The residue was 'flash distilled' in a wiped-film still at 120° C., 12 mm of mercury, and the distillate, largely dibromobenzene, was discarded. The residue was subjected to 'molecular distillation' at 120° C., 10$^{-3}$ mm of mercury. The distillate comprised the product 'bromodiphenyl methane', about 700 g (50%) being obtained. Passage of the residue of the molecular distillation through the still a second time yielded small amounts of the product.

It will be apparent to one skilled in the art that the temperatures and pressures given for the distillation at reduced pressures are only approximate, as the progress of molecular distillation is affected by the geometry of the still and the feed-rate. Both the 'Flash Distillation' and the final Molecular Distillation are carried out in a 'wiped-film' still for example of the type manufactured by Leybold-Heraeus.

When first distilled, the final product varied from water-white to lemon yellow, but darkened on exposure to light, apparently without deleterious effects to its performance in an electroviscous fluid. If required, the colour was removed by passage through activated alumina, or by distillation at atmospheric pressure, a process which did not in fact damage the material, reflecting good thermal stability. Such decolourised material in fact normally darkened again when exposed to light. However, it would appear that the darkening is due to an impurity, insofar that some samples of the material have been obtained which have lost this tendency. It is clear that the material, as normally prepared, was in fact a mixture of substances, since both by fractionation at ambient pressure and by careful molecular distillation a series of fractions of gradually increasing boiling-point and density could be obtained. It is suspected that during the primary reaction, transfer of bromine takes place from the bromobenzene, to previously formed bromodiphenyl methane, giving rise to more highly brominated species. No effect was made to obtain chemically pure materials, since it is believed that the range of species present in the final product was responsible for its particularly advantageous properties. The density of this material, as normally prepared, was about 1.45 g cm$^{-3}$, significantly higher than expected and, very conveniently, almost an exact match for the cross-linked lithium polymethacrylate solid, and hence simplifying greatly the problem of producing density matched fluids. Additionally the large number of different chemical species present lead to a very low freezing point for the product, below $-20°$ C. The viscosity of the final product as normally prepared is some 15 mPa.s at 20° C., although the higher boiling fractions increase the viscosity of some fractions. The EV performance of fluids made using this liquid is shown in Table 2 below. The combination of ease of preparation, stability, boiling point, melting point and viscosity with an average EV response appears to form the best 'envelope' of properties observed among the examples described herein.

EXAMPLES 7 and 8

Use of Friedel-Craft Reactions to join other dissimilarly substituted ring systems and thereby form asymmetrically substituted diaryl derivatives Analogous reactions to Example 6 were carried out between a halogen substituted aromatic hydrocarbon (Ar-H) and a substituted benzyl halide Ar'-CH$_2$-Y, in which Y is the halide, in the presence of aluminium chloride, to produce a halogenated diaryl methane Ar-CH$_2$-Ar'. The reactions were carried out as below.

(a) 3 mole equivalents of Ar-H were added to approximately ⅓ mole equivalent of anhydrous Aluminium Chloride. The suspension was stirred magnetically at room temperature.

(b) 1 mole equivalent of Ar'-CH$_2$-Y was slowly added to the suspension prepared as in (a) above, the addition taking approximately an hour, stirring and cooling in a water bath being maintained. When the addition was complete, the mixture was left stirring at room temperature overnight.

(c) The mixture was washed consecutively with water (1 volume), 1M sodiumhydroxide (3×1 volume) and water (3×1 volume).The organic layer was then dried by filtration through a phase-separating filter (Whatman, Type IPS).

(d) The organic mixture was then distilled in two stages, the first at atmospheric pressure to remove water and unreacted Ar-H, and the second at reduced pressure. The product was usually found to distil in the region of 200° C./4 mm of mercury after a small lower boiling fraction containing water and unreacted Ar-H.

(e) Any yellow colour in the final distilled product was removed by passing through a short column of activated alumina. Two materials were prepared in this manner using 2-ClC$_6$H$_4$- as Ar', 2-CH$_3$C$_6$H$_3$Cl (Example 7) and C$_6$H$_4$Br (Example 8) as Ar respectively. Neither of these two materials showed any sign of freezing at $-10°$ C. and both had viscosities in the region 15-20 mPa.s at 20° C. Both were suitable for use in EV fluids, Example 8 being most suitable in view of its high density.

The properties of the liquid materials produced in Examples 1-8 above may be summarized as in Table 1 below. The EV response at zero shear of fluids prepared from the liquid materials of Examples 1-8 and 30% (v/v) cross linked lithium polymethacrylate are given in Table 2. Similar data for fluids prepared from commercially available liquids and 30% cross linked lithium polymethacrylate is also given in Table 2.

TABLE 1

| EXAMPLE | R | Substituents $X^1$, $X^2$ | Substituents CH$_3$ | Density gcm$^{-3}$, 20° C. | Melting point °C. | Boiling point °C. at ( ) mm mercury | Viscosity mPa · s |
|---|---|---|---|---|---|---|---|
| 1 | CH$_2$ | $X^1 = X^2 =$ Cl<br>m + n approximately = 1 | p = q = 0 | 1.2 | — | 150 (2) | 15 at 20° C. |
| 2 | CH$_2$ | $X^1 = X^2 =$ Cl<br>m + n approximately = 2 | p = q = 0 | 1.22 | — | 200 (5) | — |
| 3 | 0 | $X^1 = X^2 =$ Cl<br>m + n approximately = 3 | p = q = 0 | 1.32 | less than 5 | 175-185 (5) | — |
| 4 | CH$_2$ | $X^1 = X^2 =$ Cl<br>m approximately = 1<br>n approximately = 1 | p = q = 0 | 1.23 | 0 | 300 (360) | 15 at 30° C. |
| 5 | CH$_2$ | $X^1 = X^2 =$ Br<br>m approximately = 1<br>n approximately = 1 | p = q = 0 | 1.64 | 4 | 174 (1) | 19 at 30° C. |
| 6 | CH$_2$ | $X^1 = X^2 =$ Br<br>m approximately = 1<br>n approximately = 0 | p = q = 0 | 1.45 | $-20$ | 120 (10$^{-3}$) | 15 at 20° C. |
| 7 | CH$_2$ | $X^1 = X^2 =$ Cl<br>m approximately = 1 | p = 1 q = 0 | 1.2 | less than $-10$ | 200 (4) | 15-20 at 20° C. |

TABLE 1-continued

| EXAMPLE | R | Substituents $X^1$, $X^2$ | Substituents $CH_3$ | Density $gcm^{-3}$, 20° C. | Melting point °C. | Boiling point °C. at ( ) mm mercury | Viscosity mPa·s |
|---|---|---|---|---|---|---|---|
| 8 | $CH_2$ | $X^1 = Br\ X^2 = Cl$ n approximately = 1 m approximately = 1 n approximately = 1 | p = q = 0 | 1.55 | less than −10 | 200 (4) | 15-20 at 20 °C. |

TABLE 2

| Liquid | S/V (Pa·mm/V) FLUID | S/V (Pa·mm/V) AROCLOR CONTROL | Eo (kV/mm) FLUID | Eo (kV/mm) AROCLOR CONTROL | P (nA/Vm) FLUID | P (nA/Vm) AROCLOR CONTROL | Q (fA/V2) FLUID | Q (fA/V2) AROCLOR CONTROL |
|---|---|---|---|---|---|---|---|---|
| EX 1 (LW) | 1.91 ± 0.28 | 2.02 ± 0.36 | 1.7 ± 0.56 | 0.88 ± 0.44 | 0.55 ± 0.75 | 1.57 ± 0.77 | 2.54 ± 0.24 | 3.71 ± 0.33 |
| EX 1 (HW) | 2.45 ± 0.55 | 1.6 ± 0.15 | 1.88 ± 0.70 | 0.92 ± 0.24 | −10.7 ± 11.9 | −2.25 ± 2.02 | 18.6 ± 4.8 | 18.2 ± 1.0 |
| EX 2 | 2.03 ± 0.4 | 1.85 ± 0.15 | 1.1 ± 0.46 | 0.96 ± 0.20 | 4.78 ± 1.78 | −1.1 ± 2.7 | 14.2 ± 1.0 | 16.8 ± 1.30 |
| EX 3 | 1.84 ± 0.15 | 2.43 ± 0.2 | 0.73 ± 0.16 | 0.32 ± 0.17 | −9.4 ± 5.8 | −2.4 ± 1.0 | 20.2 ± 2.8 | 10.5 ± 0.5 |
| EX 4 (LW) | 2.23 ± 0.2 | 1.65 ± 0.10 | 1.14 ± 0.24 | 0.76 ± 0.14 | −2.1 ± 0.70 | −0.49 ± 0.30 | 3.33 ± 0.28 | 2.63 ± 0.15 |
| EX 4 (HW) | 1.98 ± 0.13 | 1.75 ± 0.11 | 0.65 ± 0.13 | 0.45 ± 0.14 | −4.8 ± 2.6 | −1.98 ± 4.95 | 20.6 ± 1.4 | 27.2 ± 2.4 |
| EX 5 | 1.79 ± 0.04 | 1.97 ± 0.1 | 0.86 ± 0.06 | 0.55 ± 0.12 | −0.19 ± 0.50 | −0.53 ± 0.34 | 2.03 ± 0.23 | 2.31 ± 0.16 |
| EX 6 (BDM) | 2.31 ± 0.26 | " | 0.90 ± 0.28 | " | −1.16 ± 0.52 | " | 2.30 ± 0.24 | " |
| EX 7 | 2.03 ± 0.14 | " | 0.46 ± 0.16 | " | −0.74 ± 0.21 | " | 2.29 ± 0.09 | " |
| EX 8 | 1.69 ± 0.07 | " | 0.90 ± 0.11 | " | −0.75 ± 0.31 | " | 2.44 ± 0.12 | " |
| TBE | 1.57 ± 0.05 | " | 0.60 ± 0.07 | " | −0.49 ± 0.26 | " | 2.16 ± 0.12 | " |
| DPE (comp) | 1.67 ± 0.08 | " | 1.0 ± 0.16 | " | −0.26 ± 0.43 | " | 2.42 ± 0.15 | " |
| DPS (comp) | 1.78 ± 0.08 | " | 0.87 ± 0.13 | " | +0.72 ± 0.33 | " | 2.56 ± 0.13 | " |
| DDM (comp) | 2.25 ± 0.25 | " | 2.1 ± 0.38 | " | 22.7 ± 9.4 | " | 14.5 ± 3.4 | " |
| BFPM | 2.12 ± 0.13 | " | 0.96 ± 0.17 | " | −0.48 ± 0.30 | " | 2.09 ± 0.11 | " |
| DDS (comp) | 0.84 ± 0.12 | " | 2.02 ± 0.58 | " | −23.4 ± 7.7 | " | 10.81 ± 1.81 | " |
| DBDS | 1.71 ± 0.24 | " | 2.52 ± 0.58 | " | 10.11 ± 0.75 | " | 2.69 ± 0.28 | " |
| DCM | 2.09 ± 0.09 | 2.13 ± 0.11 | 1.03 ± 0.14 | 0.52 ± 0.14 | −1.17 ± 0.85 | −0.68 ± 0.27 | 3.58 ± 0.31 | 3.1 ± 0.11 |
| BBE | 1.9 ± 0.13 | " | 1.43 ± 0.21 | " | −0.07 ± 1.3 | " | 3.35 ± 0.44 | " |

NB.
EX = Example
LW = Low water content.
HW = high water content
TBE = Tribromophenyl ether
DPE = Diphenyl ether
DPS = Diphenyl sulphide
DDM = Diphenyl difluoromethane
BFPM = Bis(Fluorophenyl) methane
DDS = Dimethyl diphenoxysilane
DBDS = Dimethyl bis (2,4-dichlorophenoxy)silane
DCM = Dichlorophenyl (Chlorophenyl) methane
BBE = 1,1-Bis (Bromophenyl) ethane
Comp = comparative

I claim:

1. An electroviscous liquid comprising a hydrophilic solid and a hydrophobic liquid component wherein the hydrophobic liquid component comprises at least one diaryl derivative of general formula I

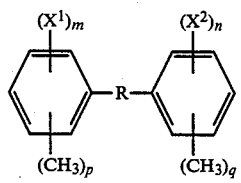

wherein R is $CY_2$, O, S, SO, $SO_2$, $SiO_2$, $SiF_2$ or $O$-$SiY_2$-O, $X^1$ and $X^2$ are either the same or different and are F, Cl or Br, each of m and n is 0, 1, 2 or 3, each of p and q is 0, 1 or 2 and Y is H, F or a methyl or ethyl group, provided that, for the said diaryl derivatives in the liquid component, the average value of (m+n) is from 1 to 3 inclusive and the average value of (p+q) is from 0 to 1 inclusive.

2. An electroviscous fluid according to claim 1 wherein R is $CH_2$, O, or S, $X^1$ and $X^2$ are the same or different and are Cl or Br, each of m and n is 0, 1, or 2, and each of p and q is 0 or 1.

3. An electroviscous fluid according to claim 2 wherein R is $CH_2$, $X^1$ and $X^2$ are Br, each of m and n is 0, 1 or 2, each of p and q is 0 and the average value of (m+n) is about 1.

4. An electroviscous fluid according to claim 1 wherein more than 80% of the at least one diaryl derivatives in the hydrophobic liquid component are asymmetrically substituted.

5. An electroviscous fluid according to claim 1 wherein the molar volume of the hydrophobic liquid component is above about 120 $cm^3$.

6. An electroviscous fluid according to claim 1 wherein the density of the hydrophobic liquid component at 20° C. is between about 1.2 and 1.8 gm $cm^{-3}$.

7. An electroviscous fluid according to claim 1 wherein the hydrophobic liquid component further comprises at least one further hydrophobic liquid selected from the group consisiting of hydrocarbons, fluorinated polymers and polychlorinated biphenyls.

8. An electroviscous fluid according to claim 1 wherein the hydrophilic solid comprises a polyhydric alcohol in particulate form.

9. An electroviscous fluid according to claim 1 wherein the hydrophilic solid comprises water-containing polymer particles having free or neutralised acid groups, provided that the polymer is not a polyhydric alcohol.

10. An electroviscous fluid according to claim 9 wherein the hydrophilic solid comprises lithium polymethacrylate (LiPM) either in cross-linked or non-cross-linked form.

11. An electroviscous fluid according to claim 10 wherein the LiPM is cross-linked with methylene bis-acrylamide (MBA).

12. An electroviscous fluid according to claim 9 wherein the fluid contains between about 25 and 35% (v/v) of the polymer particles, said particles having sizes of between about 1 and 50 microns.

13. An electroviscous fluid according to claim 7 wherein the fluorinated polymer is a polymer of trifluorovinyl chloride.

14. An electroviscous fluid according to claim 11 wherein the molar ratio of methacrylic acid content to MBA is 6 to 1.

* * * * *